United States Patent
Marple et al.

(10) Patent No.: US 7,082,811 B2
(45) Date of Patent: Aug. 1, 2006

(54) CASCADE IMPACTOR WITH INDIVIDUALLY DRIVEN IMPACTOR PLATES

(75) Inventors: Virgil A. Marple, Maple Plain, MN (US); Benjamin Y. H. Liu, North Oaks, MN (US)

(73) Assignee: MSP Corporation, Shoreview, MN (US)

( * ) Notice: Subject to any disclaimer, the term of this patent is extended or adjusted under 35 U.S.C. 154(b) by 72 days.

(21) Appl. No.: 10/910,999

(22) Filed: Aug. 4, 2004

(65) Prior Publication Data

US 2005/0028616 A1  Feb. 10, 2005

Related U.S. Application Data

(60) Provisional application No. 60/492,847, filed on Aug. 6, 2003.

(51) Int. Cl.
*G01N 1/00* (2006.01)
*G02N 1/22* (2006.01)
(52) U.S. Cl. .................... 73/28.05; 73/863.22
(58) Field of Classification Search .......... 73/363.21, 73/363.22, 363.23, 865.5, 28.05, 28, 863.21, 73/863.22, 863.23, 28.01
See application file for complete search history.

(56) References Cited

U.S. PATENT DOCUMENTS

| | | | | |
|---|---|---|---|---|
| 3,429,187 A | * | 2/1969 | Werner ................ | 73/863.21 |
| 3,518,815 A | * | 7/1970 | Peterson et al. ........ | 73/863.22 |
| 3,693,457 A | * | 9/1972 | Pilat ................... | 73/865.5 |
| 3,795,135 A | * | 3/1974 | Andersen .............. | 73/28.06 |
| 4,189,937 A | * | 2/1980 | Nelson ................. | 73/28.06 |
| 4,321,822 A | | 3/1982 | Marple et al. .......... | 73/28 |
| 4,327,594 A | * | 5/1982 | Nelson ................. | 73/863.22 |
| 4,387,603 A | * | 6/1983 | Nelson ................. | 73/863.22 |
| 4,391,151 A | * | 7/1983 | Nelson et al. .......... | 73/863.23 |
| 4,590,792 A | * | 5/1986 | Chiang ................. | 73/28.06 |
| 4,640,140 A | * | 2/1987 | Burghoffer et al. ..... | 73/863.22 |
| 6,101,886 A | * | 8/2000 | Brenizer et al. ........ | 73/863.23 |
| 6,267,016 B1 | * | 7/2001 | Call et al. ............. | 73/863.22 |
| 6,431,014 B1 | | 8/2002 | Liu et al. .............. | 73/863.22 |
| 6,517,593 B1 | * | 2/2003 | Robertson et al. ...... | 55/385.1 |
| 6,685,759 B1 | * | 2/2004 | Dahlin et al. .......... | 55/465 |

(Continued)

OTHER PUBLICATIONS

Copy of Official Search Report in counterpart foreign application No. PCT/US2004/025461, filed Aug. 6, 2004.

(Continued)

*Primary Examiner*—Hezron Williams
*Assistant Examiner*—John Fitzgerald
(74) *Attorney, Agent, or Firm*—Westman, Champlin & Kelly, P.A.

(57) ABSTRACT

A cascade impactor apparatus has a series of vertically stacked impactor housing sections. Each of the impactor housing sections has an upper portion that supports a motor for driving an impactor plate that is positioned below a nozzle through which flow passes. Each housing section also has an outlet passageway leading to a lower impactor chamber for the next in a series of impactor chambers, except the last outlet passageway is coming through a filter to exhaust. The impactor chambers are defined by a skirt that seals on the neck of the next downstream housing section. The impactor plates are each driven by a separate motor, and held onto a hub on the motor output shaft with a magnetic coupling so the plates can be removed when the housings are separated.

19 Claims, 4 Drawing Sheets

U.S. PATENT DOCUMENTS 6,695,146 B1 * 2/2004 Call et al. .................... 209/143
6,723,568 B1 * 4/2004 Liu et al. ..................... 436/174
6,729,196 B1 * 5/2004 Moler et al. ............. 73/863.22
6,826,949 B1 * 12/2004 Berndt ...................... 73/64.56
6,951,147 B1 * 10/2005 Call et al. ................ 73/863.22

OTHER PUBLICATIONS

Copy of Written Opinion of the International Searching Authority in counterpart foregin application No. PCT/US2004/025461, filed Aug. 6, 2004.

* cited by examiner

CASCADE IMPACTOR WITH INDIVIDUALLY DRIVEN IMPACTOR PLATES

This application claims priority on U.S. Provisional Application Ser. No. 60/492,847 filed Aug. 6, 2003, and the contents of which Provisional Application Ser. No. 60/492,847 are incorporated by reference.

BACKGROUND OF THE INVENTION

The present invention relates to a cascade impactor, that is, an impactor that has a number of impactor stages in flow series for classifying particles according to "cut" sizes. Each impactor stage has a nozzle plate through which particle carrying fluid passes, and has a separate rotating impactor plate positioned below each nozzle plate. Each of the impactor plates is driven by a separate motor that can be controlled as to speed.

In the prior art, rotating impactor plates in an impactor apparatus are disclosed in U.S. Pat. No. 4,321,822. The device in U.S. Pat. No. 4,321,822 has a series of impactor plates positioned side-by-side, and they are all rotated through a gear arrangement from a single motor and drive shaft.

SUMMARY OF THE INVENTION

The present invention relates to a cascade impactor having rotating impactor plates, wherein the impactor plates are individually rotational driven about an axis perpendicular to the impactor plate by a separate motor.

The cascade impactor of the present invention has a plurality of individual impactor stages, and each stage includes a nozzle and an associated impactor plate. Each impactor plate is individually rotational driven by a separate motor. The speed of rotation of the motors and the impactor plates is preferably the same for all of the plates. The motors can be powered in parallel, so they are all on or all off.

The impactor housings that are used for mounting the impactor plates and the nozzle plates through which the material carrying the particles pass, are stacked vertically and inter-fit with each other. Flow is provided from an inlet through the impactor stages in series to an outlet, and a large number of impactor stages can be utilized without substantial alteration of the construction of each of the individual impactor plates and the mounts for the impactor plate drive motors. The nozzle plates for each stage have different size orifices or a different number of nozzles from the other stages to provide a different particle cut size.

The impactor housing sections each have a flange that fits onto a neck of the next lower housing. The interfitting parts can be sealed with O-rings. The housings are stacked one on top of the other between an inlet housing and an outlet filter.

The construction of the drive to rotate the impactor plates is greatly simplified because the individual motors are readily available and relatively low cost and the impactor plates can be mounted directly on the motor shafts.

DETAILED DESCRIPTION OF THE PREFERRED EMBODIMENTS

Figure 1:
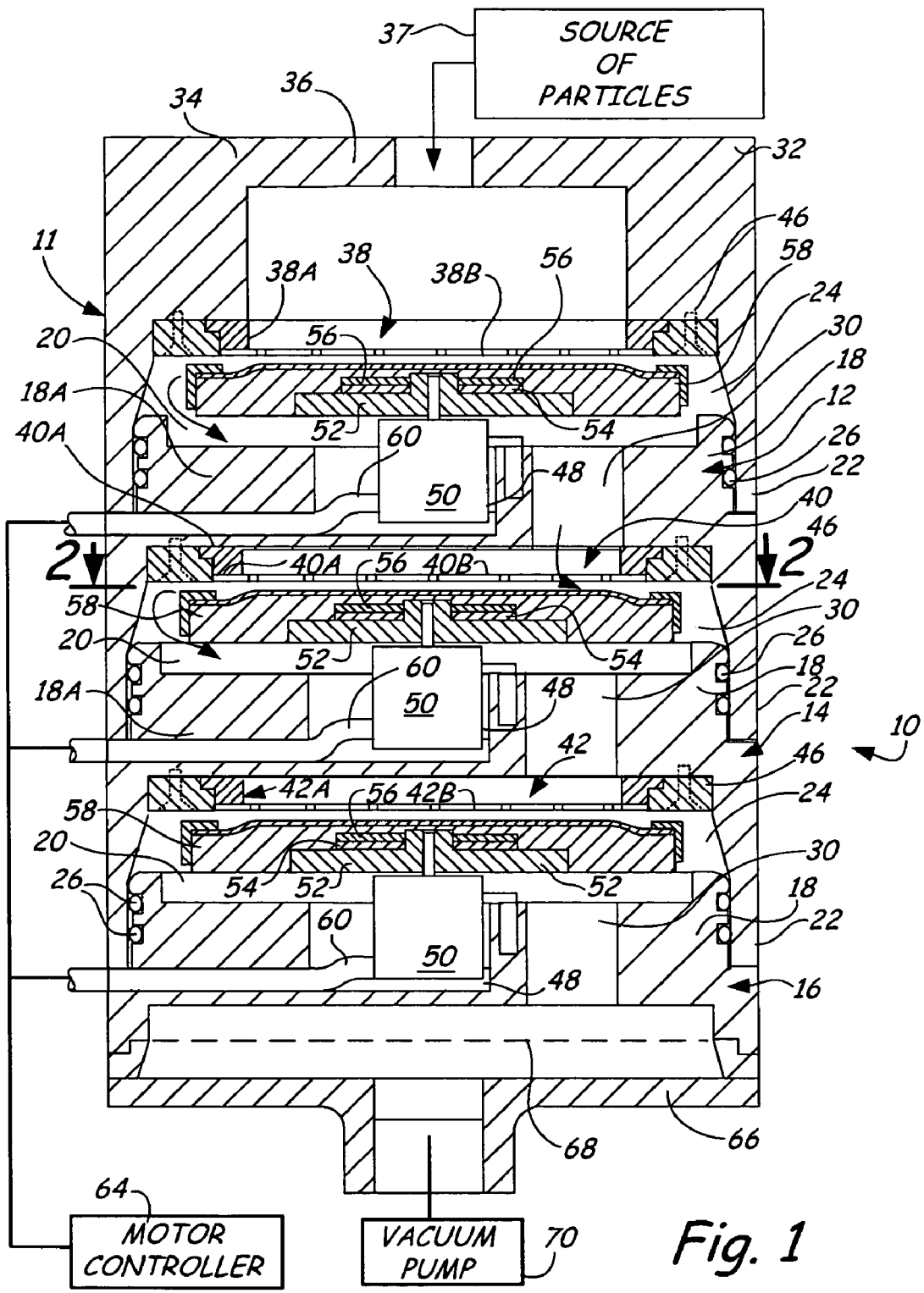
FIG. 1 is a sectional view of a cascade impactor showing only a few impactor stages for illustrative purposes, and taken as on line 1—1 in FIG. 2.
Figure 2:
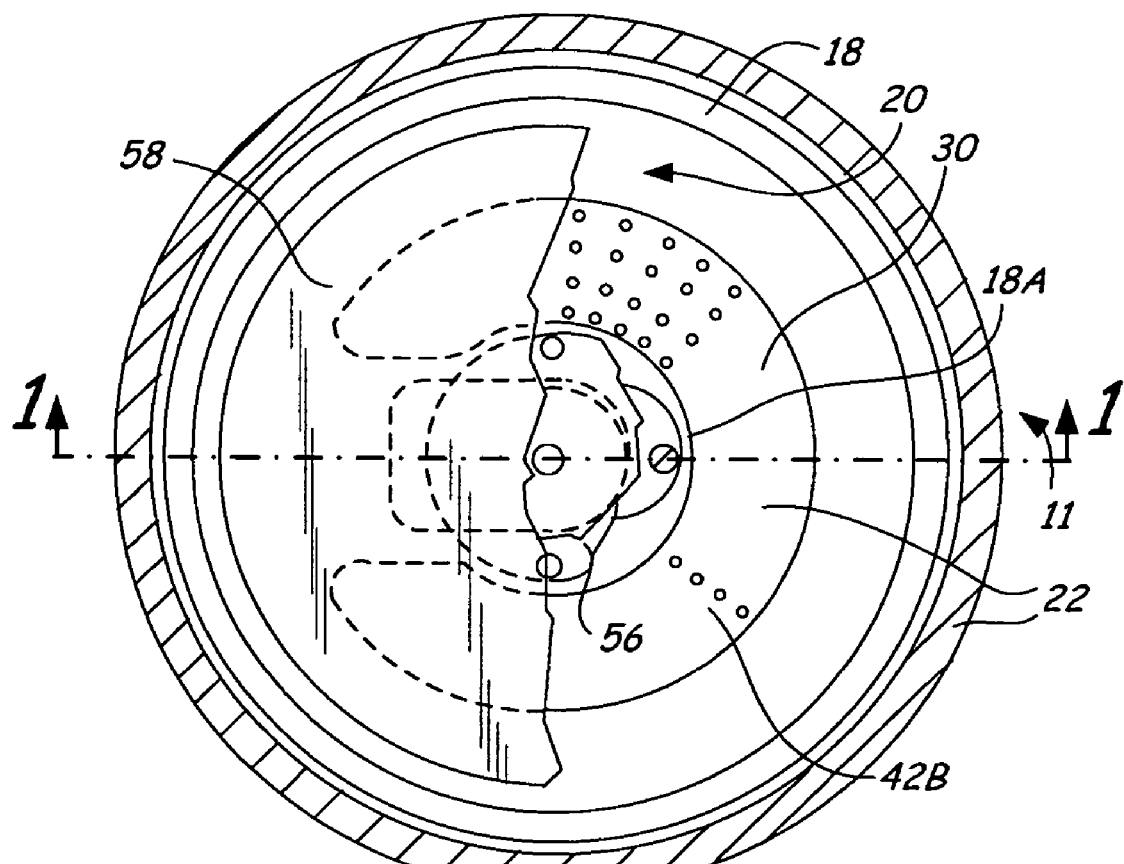
FIG. 2 is a view taken generally along the line 2—2 in FIG. 1, with parts broken away.

A multi-stage cascade impactor shown at 10 in FIG. 1 has an impactor housing 11 that is made up of a number of impactor housing sections, in this case, three sections shown at 12, 14, and 16. The housing sections are circular in cross-section, as seen in FIG. 2. Each housing includes an inlet end neck 18, and a lower skirt 22. An upper open top plenum chamber 20 is formed at the upper end of the neck 18. An interior downwardly open impactor plate chamber 24 is formed on the interior of the skirt 22. The skirt 22 of one housing section fits around the neck 18 of the next lower housing section, and O-rings 26 are provided in grooves in the neck to seal on the interior surface of the skirt.

The neck portion of each housing section has a part annular (horseshoe shaped) opening 30 (see FIG. 2) through a wall 18A that provides a passageway from an upper plenum chamber 20 down into the impactor chamber 24 of the next lower or downstream housing section.

The uppermost housing section 12 has an inlet housing 32 mounted thereon. The inlet housing 32 has a skirt 22, and an inlet chamber 34. The inlet chamber 34 in the inlet housing 32 forms an inlet plenum that has a central opening 36, which is connected to a source of particles indicated at 37. The skirt 22 of the inlet housing 32 also defines an impactor chamber 24.

Figure 4:
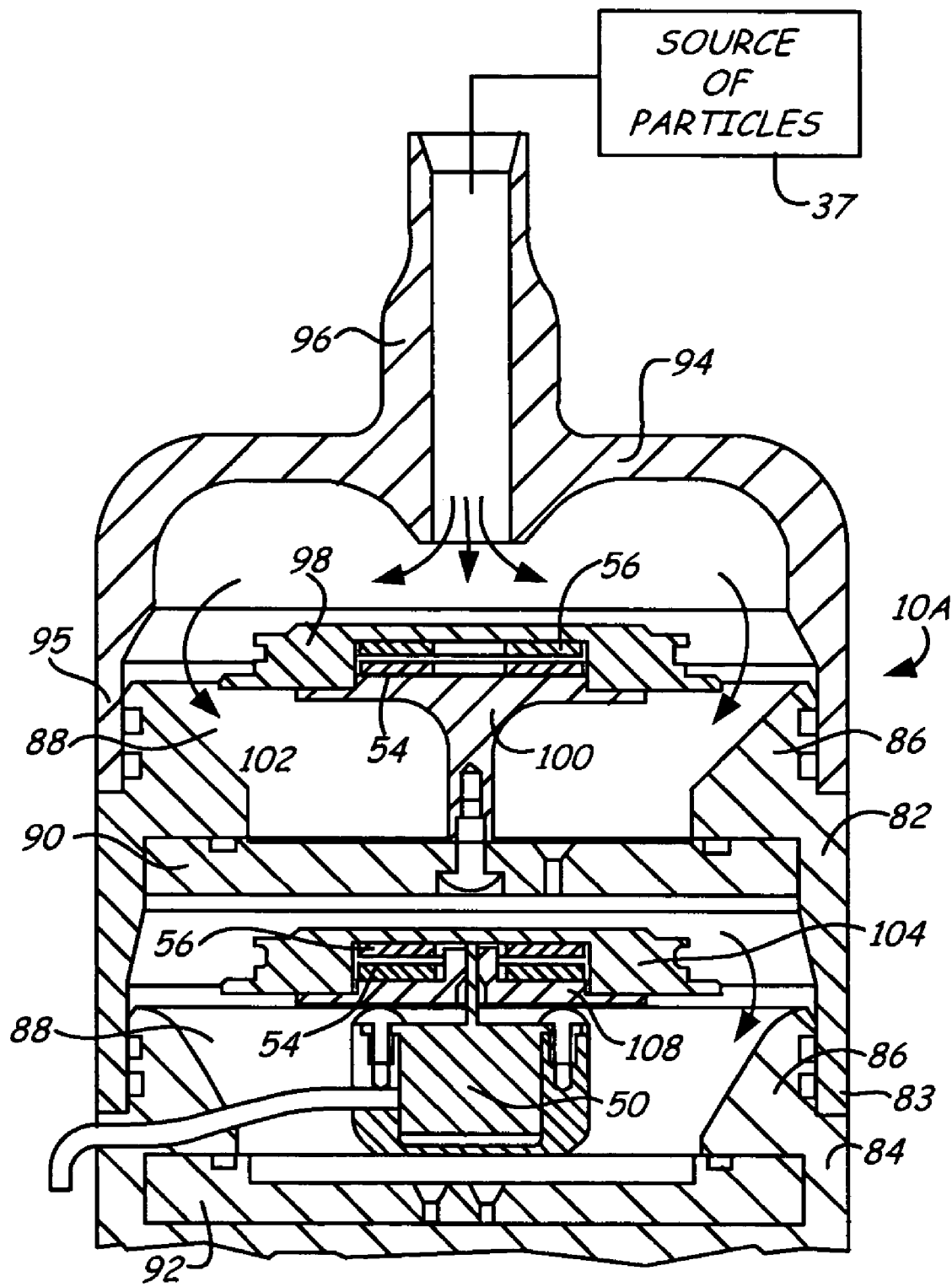
FIG. 4 is a modified inlet end configuration.

The inlet housing and the housing sections 12 and 14 illustrated each support a nozzle plate assembly 38, 40, and 42, respectively, for the three impactor stages that are illustrated. The nozzle plate 38 is a first stage nozzle, as shown, but a modified inlet is illustrated in FIG. 4.

The nozzle plate assemblies 38–42 each have an annular support ring 38A, 40A and 42A, that supports a perforated nozzle plate 38B, 40B and 42B, respectively. The nozzle plates are welded to the respective support rings, and the separate nozzle plates have progressively smaller openings therein in down stream flow direction to provide for the particle classification desired. The nozzles or openings are spaced on the nozzle plates to provide for uniform deposit particles above the cut off size on the rotating impactor plates. The lighter particles flow to the next impactor stage. These annular support rings 38A, 40A, and 42A are each held in place with a separate clamp ring 46 at each impactor stage. The clamp rings 46 are fastened at the upper part of the respective impactor chamber 24 and have shoulders that engage mating flanges on the associated annular support ring to hold the nozzle plates 38B, 40B and 42B securely in place.

Each of the housing section necks 18, in addition to having the passageway 30 therein, is provided with a motor support chamber 48 in wall sections 18A. A small electric motor 50 is mounted in each chamber 48. Each motor 50, in each of the necks 18, has a drive shaft or motor shaft extending upwardly, and each motor shaft mounts a drive hub 52. The drive hubs 52 in turn have a magnetic coupling plate 54 fixed thereon, (see FIG. 3 for a typical showing) which mates with a magnetic coupling plate 56 on a rotating impactor plate 58.

There is a separate impactor plate 58 at each of the impactor stages. The hub 52 mounted on each motor will drive magnetic coupling plates and thus drive the respective impactor plate 58 in each separate impactor stage. The motors will rotate the impactor plate at the desired rotational speed. Each impactor plate 58 is rotated about a central axis perpendicular to the plane of the plate.

An electric power coupling 60 is provided at each motor. The coupling 60 is connected to a power cable section 62 that extends out through a suitable passageway in the neck 18 of each of the housing sections. The cable 62 connects the motors in parallel and a suitable controller 64 controls the motors 50.

The lowermost impactor stage housing section which has nozzle 42A above the impactor plate mounts to a filter support 66, that supports a filter 68 in position so that the flow through the passageway 30 in the neck 18 on the filter support will pass through the filter 68. A vacuum pump 70 can be used for establishing a flow. The filter 68 can be used for collection of residual particles.

Figure 3:
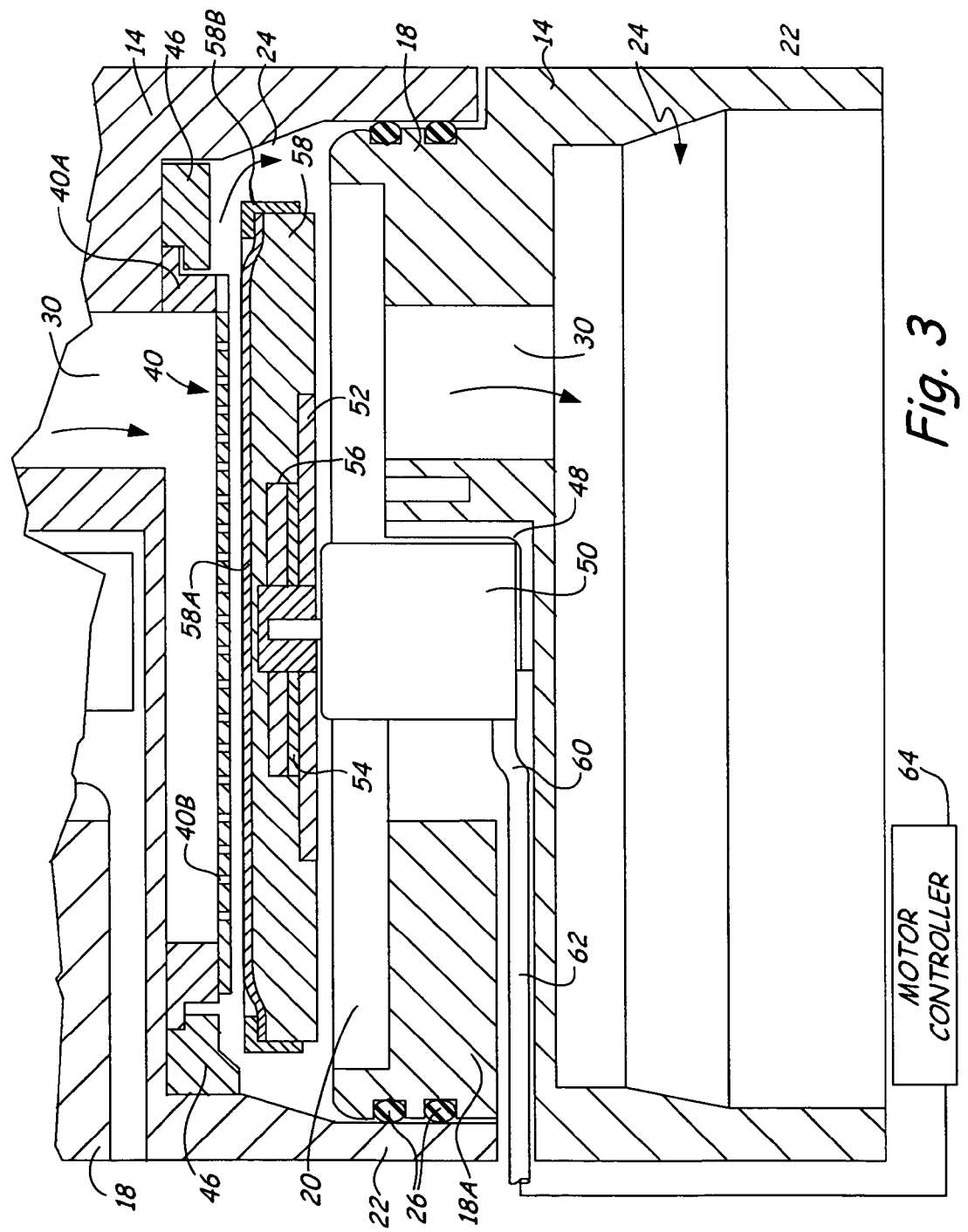
FIG. 3 is an enlarged sectional view of one impactor stage with parts in section and parts broken away.

For collection of particles and then removal for analyzing them. The impactor plates 58 as shown in FIG. 3, for example, have a cover formed of a layer 58A of aluminum foil on top of and formed over the edges of the impactor plates. The aluminum foil is held in place with a ring 58B, which slips over the peripheral edges of the respective plate 58. These foil covers are removable from the impactor plates in the laboratory. New covers are put into place for each new run.

The housing sections forming the impactor stages are frictionally held together and sealed with the O-rings 26, and when the sampling run is completed, the housing sections can be separated and the impactor plates removed. The magnetic coupling for the plates 58 makes removal an easy task. The plates 58 covered with the foil are used to carry the particles to a lab for analysis. Covers can be placed over the plates for protection.

In FIG. 4, a modified form of the impactor inlet end is shown, and a slightly modified construction of the single rotating impactor plate is also illustrated in FIG. 4.

An impactor illustrated at 10A has a number of impactor stages, but only two stages are shown. In this form of the invention, the impactor assembly 10A, that can have several impactor stages, includes impactor sections 82 and 84, which are identical, but the impactor section 84 is only partially shown. Impactor section 82 has an upper neck 86 that forms an open top plenum chamber 88. The upper necks 86 have a counter bore portion that mount nozzle plates 90 and 92 in the two sections illustrated. The nozzle plates can have suitable openings therethrough for classification. The impactor section 82 has a skirt 83 that sealingly fits over the neck 86 of impactor section 84.

An inlet housing 94 has a fitting 96 that connects to a source of particles 37 as in the first form of the invention. The housing 95 has a skirt 95 that sealingly fits over the neck 86 of upper impactor section 82. The chamber surrounded by inlet housing 94 has an impactor plate 98. Impactor plate 98 that is a fixed, non-rotating impactor plate is mounted on a pedestal 100 secured to the nozzle plate 90. The pedestal 100 carries a magnetic drive plate 54, as in the first form of the invention, and non-rotating impactor plate 98 has a magnetic drive plate 56 mounted thereon to provide a magnetic mount for the impactor plate 98, so it remains stable and can be removed for analysis of particles collected thereon. As can be seen, in this form of the invention, the fixed or non-rotating impactor plate 98 has a recess that pilots on a shoulder or flange 102 of the pedestal 100.

The inlet flow, through the opening in the fitting 96, which is established with a vacuum passes toward and then around the fixed impactor plate 98 and through the nozzle plate 90 to a rotating impactor plate indicated at 104 in the next lower stage of the cascade impactor. The impactor plate 104 is driven from a motor 50 as shown in the first form of the invention. The motor is suitably secured in the impactor assembly, and has an output shaft on which a drive hub 108, which corresponds to drive hubs 52, is mounted. The drive hub 108 has a magnetic drive plate 54 thereon. The rotating impactor plate 104 is driven by a magnetic coupling plate 56 mounted on the plate 104 in a recess on the underside that pilots on a shoulder of hub 108. The plate 104 is rotated as the impactor plates in the first form of the invention, and particles that pass through the nozzle plate 90 are classified. The larger particles are impacted on impactor plate 104, and the flow carries the rest of the particles down to the next impactor stage through the nozzle plate 92.

Thus, a first stage impactor in this form of the invention has a fixed or non-rotating impactor plate, while all of the subsequent stages have rotating impactor plates as shown in the first form of the invention.

Again, any number of impactor stages can be utilized, and each would have the individual drive motor 50 for rotating the impactor plate in all of the stages, other than the first stage, which may be a stationary plate as shown.

Each of the rotating impactor plates can have the foil covering, as illustrated in FIG. 3, and the form of the invention shown in FIG. 4 as well.

While the cascade impactor shown herein is vertically stacked for convenience, compactness and ease of operation, the individual motors 50 can drive impactor plates wherein housings having impactor chambers that are positioned side-by-side as shown in U.S. Pat. No. 4,321,822, if desired. Instead of having a number of bevel gear drives as shown therein, an individual electric motor can be mounted to drive each of those impactor plates as well.

The flow passage is established through the cascade impactor assemblies 10 or 10A, by having suitable passageways that lead to impactor nozzles, with the impactor plates immediately below the nozzle plates so that particles that are inertially separable at different stages are impacted onto the impactor plates for classification.

The ability to classify particles in particular cut sizes or ranges is well known.

The source of particles shown at 37 is a gas that carries the particles along with the gas. The flow volume can be controlled by controlling vacuum pump 70. Gas flows through the respective passageways from the inlet housings 32 or 94, through each of the impactor stage housing sections, and then through the filter to the vacuum pump. The skirt or flange portions 22, 95 and 83 that define the impactor chambers also form passageways for the flow of the particle-carrying gas from one impactor stage to the next, and through the respective nozzle plates that are aligned with the impactor plates. The impactor plates are rotated for collecting particles across the surface of the foils on the impactor plate. The foils are used on both forms of the impactor assembly as shown in FIG. 3, but are not shown in FIG. 4 for sake of clarity.

The seals provided by the O-rings 26 are sufficient to prevent leakage of the fluid flowing through the impactor, but permit the housing sections to be separated with relative ease when desired. The impactor plates are relatively small, for example on the order of 3 inches in diameter.

Although the present invention has been described with reference to preferred embodiments, workers skilled in the art will recognize that changes may be made in form and detail without departing from the spirit and scope of the invention.

What is claimed is:

1. A cascade impactor apparatus comprising a housing having a plurality of impactor chambers, a plurality of impactor plates, each impactor plate being positioned in an impactor chamber, a flow passageway formed through each chamber of the housing, an airflow source external of the housing to establish a flow through the flow passage from an inlet to an outlet, a separate nozzle associated with each impactor plate carrying flow through each separate nozzle toward the respective impactor plate, and an individual, separate motor inside the housing for each impactor plate, each motor rotating a separate impactor plate about a substantially central axis of the respective impactor plate.

2. The impactor apparatus of claim 1, wherein said impactor chambers are formed in impactor housing sections that are positioned one above the other and are sealingly connected to provide a flow passageway through the impactor housing sections.

3. The impactor apparatus of claim 2, wherein said impactor housing sections are generally circular in cross section, and include an upper neck portion, and a lower skirt portion, the skirt portion defining the impactor chamber for an impactor plate in a downstream impactor chamber with respect to flow direction in the flow passageway, said skirt portion sealing on an outer surface of the neck portion of the downstream impactor housing section.

4. The impactor apparatus of claim 3, wherein said impactor housing sections are stacked vertically when the skirt portion of one impactor housing section is engaged on the neck portion of a downstream impactor housing section.

5. The impactor apparatus of claim 3, wherein the selected number of said neck portions each have a recess for holding an electric motor to support and rotate an impactor plate, a passage defined in the neck portion leading to the impactor chamber formed by the skirt portion of the same impactor housing section, said passage forming a generally horseshoe shape partially around a periphery of the motor supported on the respective neck portion.

6. The impactor apparatus of claim 5, wherein each motor has an output shaft, a separable hub drivably mounted on the output shaft of the respective motor, each hub having a surface generally parallel to the impactor plate supported by the respective motor and perpendicular to the output shaft of that motor, and a magnetic coupling on each hub surface for supporting and driving a respective impactor plate that is associated with that motor.

7. The impactor apparatus of claim 6, wherein each magnetic coupling comprises a pair of planar magnets, one of which is mounted on the surface of the hub of the respective motor, and the other of which is mounted onto the impactor plate driven by the respective motor.

8. The impactor apparatus of claim 6, wherein the cascade impactor apparatus has an inlet chamber with a non-rotating impactor plate, and the selected number comprising all of the other impactor plates in the cascade impactor apparatus.

9. An impactor comprising a housing defining an impactor chamber having an outlet, an air flow source external of the impactor connected to generate an air flow from the inlet to the outlet, an inlet nozzle in the impactor chamber to direct fluid flow carrying particles to be classified into the impactor chamber, an impactor plate having a planar surface facing the inlet nozzle in the impactor chamber and aligned with the inlet nozzle to receive particles of size to impact upon a surface of the impactor plate, and an individual electric motor mounted inside the housing and centered on the housing and having an output shaft supporting and rotationally driving the impactor plate about an axis generally perpendicular to the impactor plate.

10. The impactor of claim 9, wherein the electric motor output shaft has a hub drivably mounted on an outer end of the output shaft, and said impactor plate is supported on said hub and driven thereby.

11. The impactor of claim 9, wherein said nozzle comprises a nozzle plate substantially parallel to the impactor plate, said nozzle plate having a plurality of openings of selected size through the nozzle plate.

12. The impactor of claim 9, wherein said nozzle plate has an annular rim, and a clampring attachable to the impactor housing to engage the nozzle plate rim and hold the nozzle plate in position, the nozzle plate being open to a flow passage on a side of the nozzle plate opposite from the impactor plate, the outlet comprising a flow passage on a side of the impactor plate opposite from the nozzle plate.

13. The impactor of claim 9, wherein the impactor plate is supported on and rotationally driven by the shaft of the electric motor through a releasable magnetic coupling for permitting removal of the impactor plate from the electric motor.

14. The impactor of claim 13, wherein said impactor plate is provided with a foil covering, and an annular ring to hold the foil covering on the impactor plate.

15. The impactor of claim 13, wherein said hub has an integral planar flange extending outwardly from a center axis of the output shaft, and said magnetic coupling comprises a pair of planar magnets, one of which is mounted on the flange, and the other of which is mounted on the impactor plate.

16. The impactor of claim 9, wherein there are a plurality of impactor chambers comprising the impactor, each of which plurality of impactor chambers has a nozzle and an impactor plate, each of the plurality of impactor plates being driven by a separate motor inside the housing.

17. The impactor apparatus of claim 16, wherein the impactor has an outlet and fluid flow through the inlet passage exhausting from the outlet passage, and a vacuum pump connected to the outlet passage to provide the fluid flow.

18. The impactor apparatus of claim 17, wherein there is a filter between the outlet passage and the vacuum pump.

19. The impactor apparatus of claim 17, and a controller for controlling the motors for driving the impactor plates.

* * * * *